United States Patent [19]

Snead

[11] Patent Number: 5,059,119
[45] Date of Patent: Oct. 22, 1991

[54] ORTHODONTIC BUCCAL TUBE WITH CONVERTIBLE COVER

[75] Inventor: Wilford A. Snead, San Dimas, Calif.

[73] Assignee: Minnesota Mining and Manufacturing Company, St. Paul, Minn.

[21] Appl. No.: 673,144

[22] Filed: Mar. 21, 1991

[51] Int. Cl.[5] .............................................. A61C 3/00
[52] U.S. Cl. ............................................ 433/17; 433/8
[58] Field of Search .................................. 433/17, 8, 13

[56] References Cited

U.S. PATENT DOCUMENTS

| | | | |
|---|---|---|---|
| 3,391,461 | 7/1968 | Johnson | 32/14 |
| 3,838,514 | 10/1974 | Polak | 32/14 A |
| 4,498,867 | 2/1985 | Kesling | 433/16 |
| 4,820,150 | 4/1989 | Pospisil | 433/17 |
| 4,927,362 | 5/1990 | Snead | 433/17 |
| 4,963,092 | 10/1990 | Snead | 433/17 |

Primary Examiner—Cary E. O'Connor
Attorney, Agent, or Firm—Gary L. Griswold; Walter N. Kirn; James D. Christoff

[57] ABSTRACT

A buccal tube used in orthodontic therapy is convertible to a bracket during later stages of treatment. The buccal tube includes two tabs initially extending toward each other from opposite sides of an arch wire slot. A prying tool placed in a slot of the buccal tube moves both of the tabs apart and bends the tabs toward recessed positions in order to open the slot and convert the buccal tube to a bracket.

7 Claims, 1 Drawing Sheet

ORTHODONTIC BUCCAL TUBE WITH CONVERTIBLE COVER

BACKGROUND OF THE INVENTION

1. Field of the Invention

This invention relates to an orthodontic molar buccal tube having a cover which may be opened to convert the tube to a bracket.

2. Description of the Related Art

In orthodontic treatment, an arch wire is placed in slots of tiny brackets that are fixed to anterior, cuspid and bicuspid teeth. The arch wire forms a track to guide movement of the teeth toward desired positions for orthodontically correct occlusion. Typically, ends of the arch wire are held by buccal tubes that are secured to molar teeth.

Convertible buccal tubes are used by orthodontists during an early stage of treatment. The tube is somewhat similar to an orthodontic bracket having a slot, but has a plate or cover to close the slot and form a tubular opening that is typically rectangular in cross-section. The plate can be removed when desired to open the slot and thereby convert the buccal tube to a bracket.

Convertible buccal tubes are often used on the first molars of younger children who do not yet have second molars. In earlier stages of treatment, the buccal tubes on the first molars serve as anchors for the terminal ends of the arch wire. When the second molars erupt, brackets or buccal tubes are mounted on the second molars to function as new anchors for the terminal ends of a longer arch wire. The cover over the arch wire slot of the buccal tubes on the first molars is removed before installation of the longer arch wire to convert the tubes to brackets and enable the orthodontist to carry out edgewise treatment mechanics on the first molars.

Buccal tubes having removable covers extending over arch wire slots are described in U.S. Pat. Nos. 3,391,461, 4,820,151 and 4,927,362, all of which are assigned to the assignee of the present invention. Other convertible buccal tubes are described in U.S. Pat. Nos. 3,838,514 and 4,498,867. The slot covers described in these patents are removable as a single piece from remaining portions of the buccal tube using a pliers-type tool, a prying device or some other type of tool when it is desired to convert the buccal tube to a bracket. The cover shown in U.S. Pat. No. 4,927,362 is integral with remaining portions of the bracket and is removed by shearing the cover along lines of weakness next to sidewalls of the arch wire slot.

It is possible, however, for the cover to be dropped into the oral cavity during conversion of such buccal tubes to brackets. For example, an orthodontist using a pliers-type tool may unintentionally loosen the grip on the tool handles during or after the conversion, causing the cover to drop from the jaws of the tool. When using a prying device, the cover may drop into the oral cavity if the cover is separated from the buccal tube before being grasped or otherwise retained. A cover that has been dropped in the oral cavity often can be retrieved, but such occurrences represent an inconvenience both to the orthodontist as well as to the patient.

SUMMARY OF THE INVENTION

The present invention relates to a convertible orthodontic buccal tube for mounting on a molar tooth, and includes a tooth-facing base. A body extending from the base has spaced apart occlusal and gingival portions. The body includes an arch wire slot located between the occlusal and gingival portions and has a side remote from the base. A cover includes a first tab integrally connected to the occlusal portion and a second tab integrally connected to the gingival portion. The first tab and the second tab extend toward each other and across at least a portion of the slot. The cover is made of an elastically deformable material that enables the first tab to be moved in an arc toward a position facing the occlusal portion and also enables the second tab to be moved apart from the first tab in an arc toward a position facing the gingival portion in order to open the slot.

Both the first tab and the second tab remain connected to the buccal tube as the tube is converted to a bracket. As such, the likelihood of the cover falling into the oral cavity is substantially eliminated. Additionally, the orthodontist need not be concerned with grasping the cover during the conversion operation.

DESCRIPTION OF THE PREFERRED EMBODIMENT

Figure 1:
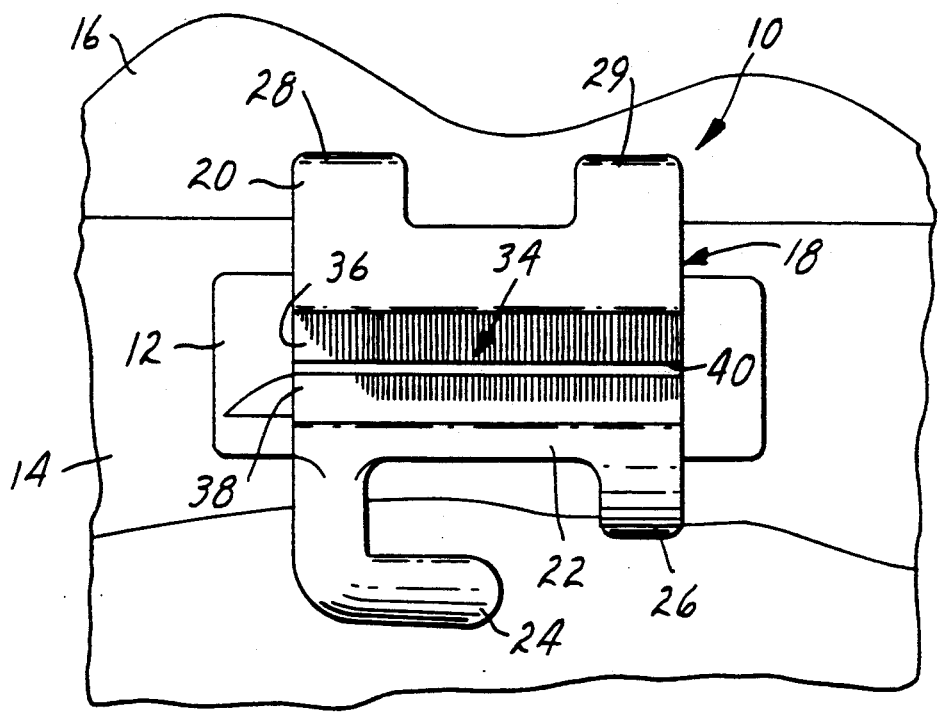
FIG. 1 is an elevational view in a lingual direction of a buccal tube of the present invention mounted on a band surrounding a first molar of the lower jaw.
Figure 2:
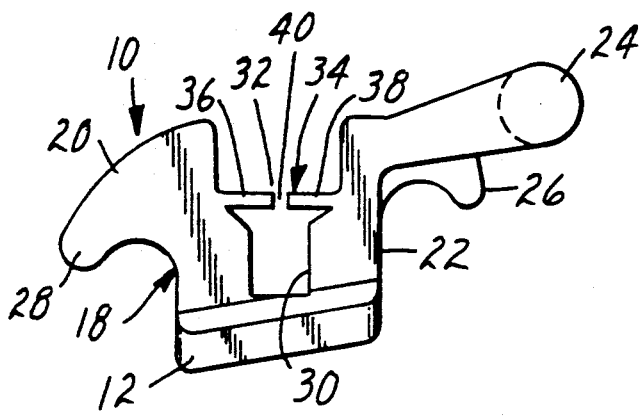
FIG. 2 is a side view taken in a distal direction of the buccal tube alone shown in FIG. 1.
Figure 3:
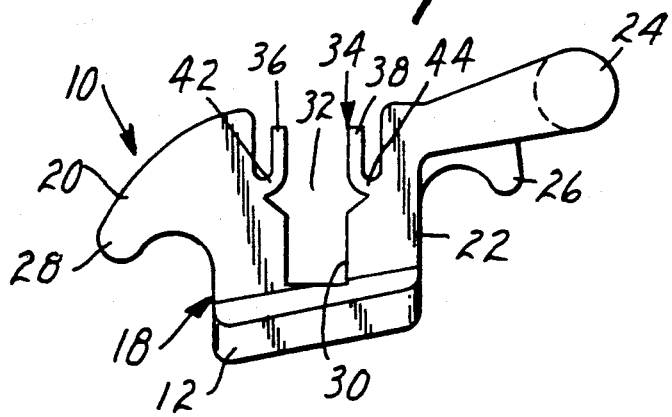
FIG. 3 is a view somewhat similar to FIG. 2 except that a cover of the buccal tube has been opened to convert the buccal tube to a bracket.

An orthodontic buccal tube 10 in accordance with the invention is illustrated in FIGS. 1-3 and includes a base 12 that is welded onto a band 14 encircling a lower first molar tooth 16. The tube 10 also includes a body 18 that is integrally connected to the base 12 and extends outwardly in a buccal direction (i.e., toward the cheeks).

The body 18 has an occlusal portion 20 and a gingival portion 22 spaced apart from the occlusal portion 20. The gingival portion 22 includes a mesial hook 24 and a distal tiewing 26. The occlusal portion 20 includes a mesial tiewing 28 and a distal tiewing 29.

An elongated arch wire slot 30 extends in a mesial-distal direction across the body 18 between the occlusal portion 20 and the gingival portion 22. The arch wire slot 30 has a rectangular cross section that is closely sized to the dimensions of the expected arch wire. In this manner, bends or twists placed in the arch wire can function to urge the tube 10 and therefore the tooth 16 toward a desired position according to edgewise therapy.

A buccal side 32 of the arch wire slot 30 is remote from the base 12, and is initially closed to a substantial extent by a cover 34. The cover 34 includes a first tab 36 that is integrally connected to the occlusal portion 20, and a second tab 38 that is integrally connected to the gingival portion 22. As illustrated in FIG. 2, the first tab 36 and the second tab 38 initially extend toward each other from the portions 20, 22, and initially lie in a common plane that is parallel to the bottom of the slot 30 next to the base 12 and perpendicular to the sides of the slot 30 adjacent the portions 20, 22. The tabs 36, 38 are the same size and have the same cross sectional area when looking in a lingual direction toward the buccal tube 10 as shown in FIG. 1.

A space 40 extends along the length of the slot 30 in a central area of its buccal side 32, equidistant from the occlusal portion 20 and the gingival portion 22. In the embodiment shown in the drawings, the space 40 extends the entire length of the slot 30 and completely separates the first tab 36 and the second tab 38. However, the cover 34 could also be made by providing a line of weakness between the tabs 36, 38 such as a relatively thin, frangible portion that is integrally connected to the first tab 36 and the second tab 38 along the entire length of the tabs 36, 38, or by a series of one or more frangible portions interspersed with spaces between the tabs 36, 38.

The tabs 36, 38 are made of an elastically deformable material that enables the first tab 36 to be moved apart from the second tab 38 in order to open the slot 30 and convert the buccal tube 10 to a bracket. As shown in FIG. 3, the first tab 36 is movable in an arc toward a position facing the occlusal portion 20. The second tab 38 is movable in an arc (that is opposite to the rotational direction of movement of the first tab 36) toward a position facing the gingival portion 22.

To open the cover 34 and convert the buccal tube 10 from the configuration shown in FIG. 2 to the configuration shown in FIG. 3, a prying tool is inserted in the arch wire slot 30 and manipulated to bend the tabs 36, 38 outwardly. An improved tool to open the cover 34 is described in my U.S. Pat. No. 4,669,979. The tabs 36, 38 in the orientation depicted in FIG. 3 have been elastically deformed (i.e., deformed past the yield point of the material) and thereafter remain stationary in the open position facing the portions 20, 22.

Importantly, the first tab 36 is connected to the occlusal portion 20 within a recess 42 of the occlusal portion 20 that is located outwardly in an occlusal direction from the occlusal side of the arch wire slot 30. Similarly, the second tab 38 is connected to the gingival portion 22 in a recess 44 of the gingival portion 22 that is located outwardly in a gingival direction from the gingival side of the arch wire slot 30. Consequently, both of the tabs 36, 38 can be rolled back when bent to an out-of-the-way orientation in order to avoid interfering with insertion of an arch wire into the arch wire slot 30.

Advantageously, the length of the tabs 36, 38 when bent to their respective orientations as shown in FIG. 3 is less in a buccal-lingual direction than the buccal-lingual dimension of the recesses 42, 44 between the outwardmost buccal side of the portions 20, 22 and the area where the tabs 36, 38 connect with the portions 20, 22. As a result, the tabs 36, 38 when bent to open the slot 30 do not protrude outwardly from the portions 20, 22 and do not irritate the patient's cheeks or interfere with other articles used in the orthodontic treatment. Also, the space 40 between the tabs 36, 38 facilitates good oral hygiene by providing an opening from which food particles may escape from the slot 30 when the cover 34 is in the closed position shown in FIG. 2.

Another important feature of the invention is the economy in manufacturing that is achieved by making the cover 34 an integral part of the buccal tube 10. The buccal tube 10 may be made as a cast or machined structure. Preferably, the buccal tube 10 is made using a sintering technique wherein the entire buccal tube 10 is initially formed as a pressed "green" preform of metal powder mixture that has been mixed with a binder to initially hold the powder together. Heating of the preform volatilizes the binder and sinters the metal to yield the final product. The powder mixture is preferably 91.5 percent by weight of a Type 316L stainless steel powder (Anzal Nyby) that is blended with 8.5 percent by weight of a thermoplastic binder made from waxes, polypropylenes, stearic acid and flow aiding agents. The preform is heated in a series of steps to a temperature of 700° F. (370° C.) to volatize the binder, and then heated during an additional series of steps to an ultimate temperature of 2300° F. (1260° C.) to sinter the powder.

The tabs 36, 38 have a thickness in the range of 0.006 inch (0.15 mm) to 0.008 inch (0.20 mm) and have sufficient strength to remain stationary and closed in the orientation shown in FIG. 2 while encountering forces subjected to the buccal tube 10 by the arch wire. However, the tabs 36, 38 can be elastically deformed without undue effort when desired by using a prying tool.

I claim:

1. A convertible orthodontic buccal tube for mounting on a molar tooth comprising:

a tooth-facing base;

a body extending from the base and having spaced apart occlusal and gingival portions, said body including an arch wire slot located between the occlusal and gingival portions and having a side remote from said base; and a cover including a first tab integrally connected to said occlusal portion and a second tab integrally connected to said gingival portion, said first tab and said second tab extending toward each other and extending across at least a portion of said slot, said cover being made of an elastically deformable material enabling said first tab to be moved in an arc toward a position facing said occlusal portion and enabling said second tab to be moved apart from said first tab in an arc toward a position facing said gingival portion to thereby open the slot.

2. The buccal tube of claim 1 including a space between said first tab and said second tab.

3. The buccal tube of claim 2 wherein said space extends substantially along the entire extent of said slot.

4. The buccal tube of claim 1 wherein said first tab and said second tab have approximately the same area when viewed in a direction toward the slot before the slot is opened.

5. The buccal tube of claim 1 wherein said occlusal portion has a recess for receiving said first tab, and wherein said gingival portion has a recess for receiving said second tab.

6. The buccal tube of claim 1 wherein said occlusal portion and said gingival portion extend, past said first tab and said second tab when said slot is opened.

7. The buccal tube of claim 1 wherein said base in integral with said body.

* * * * *